United States Patent

Sasse

[11] Patent Number: 5,135,979
[45] Date of Patent: Aug. 4, 1992

[54] POLYMERIC WEB COMPOSITIONS FOR USE IN ABSORBENT ARTICLES

[75] Inventor: Philip A. Sasse, Alpharetta, Ga.

[73] Assignee: Kimberly-Clark Corporation, Neenah, Wis.

[21] Appl. No.: 715,944

[22] Filed: Jun. 14, 1991

Related U.S. Application Data

[62] Division of Ser. No. 598,276, Oct. 16, 1998, Pat. No. 5,063,272.

[51] Int. Cl.$^5$ .......................... C08L 33/06; C08K 5/05
[52] U.S. Cl. .................................................... 524/377
[58] Field of Search ........................................... 524/377

[56] References Cited

FOREIGN PATENT DOCUMENTS 371679 6/1990 European Pat. Off. .

*Primary Examiner*—Joseph L. Schofer
*Assistant Examiner*—Jeffrey T. Smith
*Attorney, Agent, or Firm*—Gregory E. Croft

[57] ABSTRACT

The properties of (meth)acrylic ester/(meth)acrylic acid copolymer webs, such as films and nonwovens, are improved by blending the ester/acid copolymer with polyethylene glyocl. The polymer blend provides a polymeric material which is useful for making personal care porducts such as diapers and feminine pads in that it can be made water-soluble while exhibiting other properties which are necessary for adequate product performance.

7 Claims, No Drawings

POLYMERIC WEB COMPOSITIONS FOR USE IN ABSORBENT ARTICLES

This is a divisional application of copending application Ser. No. 07/598,276, filed on Oct. 16, 1990 now U.S. Pat. No. 5,063,272.

BACKGROUND OF THE INVENTION

In the production of personal care products, a number of different components and materials are required to construct the products. In the case of diaper manufacture, for example, these components include a backing material, which is a film, and an inner liner, which is typically a nonwoven web. Also, composite structures of synthetic and natural fibers have utility as absorbent media in a variety of personal care products. These various synthetic components are typically made from thermoplastic polymers such as polyethylene or polypropylene. However, with a greater emphasis being placed on protecting the environment today, there is a need to develop materials which are more compatible with existing and developing waste technologies while still delivering the performance consumers have come to expect.

Copolymers of (meth)acrylate esters and (meth)acrylic acid are of environmental interest because of their solubility in alkaline solutions or upon prolonged exposure to moisture, even though they are relatively hydrophobic. Unfortunately, the physical properties which make these materials desirable from an environmental standpoint can make them unsuitable for personal care products. In particular, films made from these polymers in contact with synthetic urine for a period greater than one hour will become hydrated, weak and sticky. This is obviously unacceptable for use in diapers, for example. Films made from these polymers also suffer from a lack of toughness and tear resistance. Films and nonwovens made from these copolymers are somewhat sticky and tend to stick or "block" in roll form. In addition, dimensional stability and aesthetic properties of these materials are also poor. Finally, the viscosity of these polymers in the temperature ranges appropriate for the production of nonwovens is too high to be compatible with certain nonwoven processes.

Therefore there is a need for copolymers of (meth)acrylate esters and (meth)acrylic acid which have modified properties suitable for use as components in personal care products.

SUMMARY OF THE INVENTION

It has now been found that copolymers of (meth)acrylate esters and/or (meth)acrylic acid can be modified with additional materials to provide polymeric webs having improved properties suitable for use in personal care products. More specifically, it has been discovered that polyethylene glycol, when blended with such ester-/acid copolymers, imparts reduced viscosity and increased processability in meltblown and similar processes. In addition, the webs produced have a measure of elasticity and can be stretched with recovery. Furthermore, said polymeric webs can be heat treated to induce a reaction between the blended polymers, thus further altering the characteristics of the web.

Hence, in one aspect, the invention resides in a composition of matter comprising a polymeric blend of from about 60 to about 95 weight percent of a (meth)acrylate ester/(meth)acrylic acid copolymer and from about 5 to about 30 weight percent polyethylene glycol.

In another aspect, the invention resides in a polymeric web comprising a blend of from about 60 to about 95 weight percent of a (meth)acrylate ester/(meth)acrylic acid copolymer and from about 5 to about 30 weight percent of a polyethylene glycol. The relative proportions of the two polymers will depend upon the desired properties of the product into which they are to be made. For use in making nonwoven webs, such as meltblown webs, it is preferred that the copolymer blend contain from about 70 to about 90 weight percent of the ethyl acrylate/methacrylic acid copolymer and from about 5 to about 20 weight percent of the polyethylene glycol.

In a further aspect, the invention resides in an absorbent article having an outer cover, an absorbent core, and an inner liner, wherein said absorbent core comprises a composite structure including a polymeric web as described herein. Suitable absorbent articles particularly include diapers and sanitary napkins.

The ethyl acrylate/methacrylic acid copolymer that is most preferred has a 4:1 ratio of the two comonomers by weight. The weight average molecular weight is about 150,000, with a melt flow rate of about 7 grams per 10 minutes, as measured at 170° C. using a 2160 g weight and a 2.1 mm by 8 mm capillary. Clearly, however, many similar copolymers can be prepared that will provide similar attributes and can be substituted for the most preferred copolymer in these compositions. For example, any other (meth)acrylate ester derived from an alcohol having from 1 to 18 carbon atoms can be substituted for all or part of the ethyl acrylate. Such substitutions can lead to enhancement of particular properties for specific material applications. The manufacture of such copolymers is described in U.S. Pat. No. 4,870,148 to RB Kunststoffpatent-Verwertugs AG and Belland AG, both of Switzerland, issued Sep. 26, 1989, which is herein incorporated by reference. Such copolymers are commercially available from Belland AG, and the most preferred copolymer is available as product code "GBC 2630".

Suitable polyethylene glycols are available commercially from Union Carbide Corporation, Tarrytown, N.J., under the tradename CARBOWAX ®; most suitable are product code numbers "3350" and "8000."

Blends of the two polymers can be prepared by mixing the desired weight ratio of the polymer pellets and blending them using any standard equipment commonly used for blending thermoplastic polymers under conditions of heat and high shear. These include the Banbury ® type of intensive production mixer (Farrel Corp, Ansonia, Conn.) and both single- and twin-screw compounding extruders, which can utilize high-shear mixing screws, co-rotating kneading blocks, etc.

Processing characteristics of the polymer blends described herein can be modified by the incorporation of lubricants or slip agents into the blends. Additives of other types normally used in polymer blends can also be incorporated to provide specific properties as needed, such as antistatic agents, pigments or other colorants, and the like. Each of these additive types are generally used in small amounts, usually about 5 percent or less.

Nonwoven webs of the two polymers can be prepared by extrusion of the blend through a plurality of capillaries, producing a series of filaments. These filaments can be quenched and attenuated into fibers by an accelerating gas stream. The fibers can be collected on a moving surface, where they are deposited by the gas stream in a random fashion. Passing the resulting batt through a pair of heated rolls bonds the fibers together into an integral web. Alternatively, a hot gas stream may be used to attenuate and break the filaments in the molten state. These discontinuous fibers can be collected on a moving surface, where they will lay down in a random, entangled manner, producing an integral web. Suitable nonwoven webs include, without limitation, meltblown webs, spunbonded webs, and coform webs (meltblown webs in which a second fiber source, such as cellulose fibers, is blown into the primary meltblown fiber stream prior to deposition onto the collecting surface). All of such webs are known in the nonwovens art.

EXAMPLE

Preparation of Polymer Blend and Nonwoven Web V

A copolymer blend containing 80% GBC 2630 AA (a 4.3:1 ethyl acrylate/methacrylic acid copolymer with no additives), and 20% CARBOWAX ® 3350 (Union Carbide, polyethylene glycol of molecular weight 3000-3700) was prepared using a ¾" single-screw compounding extruder with a single mixing section and L/D of 26:1. Strands were generated through a dual-strand die at 160° C., allowed to air cool, and pelletized.

Intrinsic viscosity of this blend was measured using a capillary rheometer with a capillary diameter of 0.0202 inches and L/D ratio of 4.89. The viscosity of the blend was 410 poise at 170° C. and 1075 $s^{-1}$. The unblended ethyl acrylate/methacrylic acid copolymer had a viscosity of 1178 poise under the same conditions. It was found that the blended polymers increased in viscosity over time when heated to 400° F., apparently due to a reaction in which the poly(ethylene glycol) grafts to the ethyl acrylate/methacrylic acid copolymer.

This blend was processed through a heated piston apparatus to force the molten blend through a 1 mm orifice at a temperature of 385° F. The filament formed was attenuated using hot air and deposited randomly on a moving collection wire, forming a web with some integrity. This polymer blend and forming method can be used to produce composite structures (coforms) suitable for a variety of personal care absorbent products. The composite is soluble and dispersible on immersion in a basic solution.

It will be appreciated by those skilled in the art that the foregoing example, given for purposes of illustration, is not to be construed as limiting the scope of this invention.

I claim:

1. A polymeric web comprising a blend of from about 60 to about 95 weight percent of a copolymer of a (meth)acrylate ester and (meth)acrylic acid and from about 5 to about 50 weight percent of polyethylene glycol.

2. The web of claim 1 wherein the (meth)acrylate ester is ethyl acrylate.

3. The web of claim 2 wherein (meth)acrylic acid is methacrylic acid.

4. The web of claim 3 wherein the copolymer of ethyl acrylate and methacrylic acid comprises about 80 weight percent ethyl acrylate moieties and about 20 weight percent methacrylic acid moieties.

5. The web of claim 3 comprising from about 70 to about 90 weight percent of a copolymer of ethyl acrylate and methacrylic acid and from about 5 to about 30 weight percent of polyethylene glycol.

6. The web of claim 3 comprising about 80 weight percent of a copolymer of ethyl acrylate and methacrylic acid and about 20 weight percent polyethylene glycol.

7. The web of claims 1, 2, 3, 4, 5 or 6 wherein the web is a nonwoven web.

* * * * *